United States Patent
Hamill

(10) Patent No.: US 11,324,472 B2
(45) Date of Patent: May 10, 2022

(54) ENERGY-BASED SCATTER CORRECTION FOR PET SINOGRAMS

(71) Applicant: Siemens Medical Solutions USA, Inc., Malvern, PA (US)

(72) Inventor: James Hamill, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 231 days.

(21) Appl. No.: 16/946,307

(22) Filed: Jun. 16, 2020

(65) Prior Publication Data

US 2021/0059629 A1 Mar. 4, 2021

Related U.S. Application Data

(60) Provisional application No. 62/891,540, filed on Aug. 26, 2019.

(51) Int. Cl.
| | |
|---|---|
| *A61B 6/00* | (2006.01) |
| *A61B 6/03* | (2006.01) |
| *G01T 1/29* | (2006.01) |
| *G06T 11/00* | (2006.01) |
| *G06T 5/40* | (2006.01) |
| *G06T 7/00* | (2017.01) |

(52) U.S. Cl.
CPC ............ *A61B 6/5282* (2013.01); *A61B 6/037* (2013.01); *A61B 6/583* (2013.01); *G01T 1/2985* (2013.01); *G06T 5/40* (2013.01); *G06T 7/0012* (2013.01); *G06T 11/005* (2013.01); *G06T 2207/10104* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 7,312,455 B2* | 12/2007 | Manjeshwar | A61B 6/037 250/363.03 |
| 7,714,291 B2 | 5/2010 | Thielemans et al. | |
| 9,872,664 B1 | 1/2018 | Jin et al. | |
| 2010/0086101 A1 | 4/2010 | Thielemans et al. | |
| 2011/0150181 A1* | 6/2011 | Cook | G01T 1/1648 378/86 |
| 2015/0289832 A1* | 10/2015 | Bal | A61B 6/5264 600/407 |
| 2017/0061629 A1* | 3/2017 | Zhu | G06T 11/005 |

OTHER PUBLICATIONS

Bendriem, B., et al. "A PET scatter correction using simultaneous acquisitions with low and high lower energy thresholds." 1993 IEEE Conference Record Nuclear Science Symposium and Medical Imaging Conference. IEEE, 1993.
Grootoonk, S., et al. "Correction for scatter using a dual energy window technique with a tomograph operated without septa." Conference Record of the 1991 IEEE Nuclear Science Symposium and Medical Imaging Conference. IEEE, 1991.
Guérin, Bastien, and Georges El Fakhri. "Novel scatter compensation of list-mode PET data using spatial and energy dependent corrections." IEEE transactions on medical imaging 30.3 (2010): 759-773.
Popescu, Lucretiu M., et al. "PET energy-based scatter estimation and image reconstruction with energy-dependent corrections." Physics in Medicine & Biology 51.11 (2006): 2919.

* cited by examiner

*Primary Examiner* — Hoon K Song

(57) ABSTRACT

A method of estimating energy-based scatter content in PET list-mode data is provided.

25 Claims, 6 Drawing Sheets

ENERGY-BASED SCATTER CORRECTION FOR PET SINOGRAMS

CROSS-REFERENCE TO RELATED APPLICATIONS

This application claims priority under 35 U.S.C. § 119(e) to U.S. Provisional Application No. 62/891,540, filed Aug. 26, 2019, the entire contents of which are incorporated herein by reference.

FIELD

The present disclosure generally relates to nuclear medical imaging, and in particular to methods and systems for determining scatter correction in PET 3D TOF sinograms.

BACKGROUND

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred. An example of a PET method and apparatus is described in U.S. Pat. No. 6,858,847, which patent is incorporated herein by reference in its entirety.

After being integrated and sorted into LORs defined by the positions of the detectors in the PET camera, the coincidence event data are used to reconstruct a three-dimensional distribution of the positron-emitting radionuclide within the patient. In two-dimensional PET, each 2D transverse (perpendicular to the axis of the PET scanner) section or "slice" of the radionuclide distribution is reconstructed independently of adjacent sections, using only LORs that are (approximately) perpendicular to the axis of the scanner (referred to as the z axis). In fully three-dimensional PET, nearly all the LOR data are used for the reconstruction. The positions of these LORs in space are characterized by their radial distance, s, from the z axis, their azimuthal angle, $\Phi$, around the z axis, their polar angle, $\Theta$, with respect to the z axis, and the z position of their closest approach to the z axis. These LOR data are typically arranged into a set of "sinograms", $p(s, \Phi; \Theta, z)$, which, for fixed values of $\Theta$ and z, represents a two dimensional parallel projection of the three dimensional radionuclide distribution within the patient. All of the LORs in the sinogram $p(s, \Phi)$ having fixed values of $\Theta$ and z are essentially co-planar. In this format, a single fixed point in the emitter distribution $f(x,y,z)$ that falls within this $(\Theta, z)$ plane traces a sinusoid in the sinogram. In each sinogram, there is one row containing the LORs for a particular azimuthal angle $\Phi$; each such row corresponds to a one-dimensional parallel projection of the tracer distribution at a different projection angle.

An event is registered if both crystals detect an annihilation photon within a coincidence time window $\tau$ (e.g., on the order of 4-5 ns), depending on the timing properties of the scintillator and the field of view. Aside from the effect of photon scatter, as discussed below, a pair of detectors is sensitive only to coincidence events originating in the volume between the two detectors, thereby eliminating the need for physical collimation, and thus significantly increasing sensitivity. Accurate corrections can be made for the self-absorption of photons within the patient (i.e., attenuation correction) so that accurate measurements of tracer concentration can be made.

The number of time coincidences detected per second within a field of view (FOV) of a detector is the count rate of the detector. The time required for a gamma photon to travel from its point of origin to a point of detection is referred to as the time of flight, or TOF, of the gamma photon. TOF is dependent upon the speed of light c and the distance traveled. A time coincidence, or coincidence event, is identified if the time difference between the arrival of signals in a pair of oppositely disposed detectors is within the coincidence time window $\tau$. In conventional PET, the coincidence detection time window $\tau$ is wide enough so that an annihilation event occurring anywhere within the object would produce annihilation gamma photons reaching their respective detectors within the coincidence window. Coincidence time windows of 4.5-12 nsec are common for conventional PET, and are largely determined by the time resolution capabilities of the detectors and electronics.

In contrast to conventional PET, TOF-PET is based on recording the difference $\Delta t$ between the detection times of the two gamma photons arising from the positron annihilation event in sub-intervals of the total coincidence window $\tau$. This measurement allows the annihilation event to be localized along the LOR with a resolution of about 30-180 mm FWHM, assuming a time resolution of 200-1200 ps (picoseconds). Though less accurate than the spatial resolution of the scanner, this approximate localization is effective in reducing noise contributions both from random coincidence events and from scattered and non-scattered photon coincidences that actually originated elsewhere in the object. This improves both the stability of the reconstruction and the signal-to-noise ratio in the final image, especially when imaging large objects. TOF-PET may increase image SNR by a factor of 2 or more compared to conventional PET.

3D PET scanners currently constitute a large percentage of the total market for PET imaging. In 3D PET scanners, scattered events (i.e., annihilation photons undergoing Compton scattering before reaching the detector) may represent a large portion of the measured data (e.g., up to 50% or more in clinical studies). An example of techniques to correct for such scattering in TOF PET utilizing a single scatter simulation (SSS) algorithm is disclosed in U.S. Pat. No. 7,397,035.

However, the current scatter correction methods using primarily SSS algorithm to correct PET scan data for scatter effects have some room for improvement. For example, the scatter correction data is acquired by CT scan modality performed before the PET scan. Thus, there is a time delay between the acquisition of the CT scan data used to estimate the scatter effects and the acquisition of the PET scan data.

Therefore, there is a need for an improved scatter correction for TOF-PET data.

SUMMARY

According to one aspect of the present disclosure, a method of estimating scattered radiation in a PET scanner that records the energy of each detected photon, in the case when both scattered and non-scattered radiation is present is provided. The method comprises: (a) acquiring scatter-free PET scan data using a substantially scatter-free source phantom in air, wherein the PET scan data comprises PET list-mode data; (b) quantifying energy signals of the non-scattered radiation based on the acquired scatter-free PET scan data; (c) modeling the scattered radiation based on the spectrum of non-scattered radiation with a reduction of the energy signal and a modification to the spectrum's shape; (d) acquiring scan data representative of a targeted patient tissue region using a PET scanner, wherein the scan data comprises PET list-mode data; (e) quantifying the distribution of energy signals in the PET list-mode data as 2D histograms representing A crystal energy vs. B crystal energy; (f) automatically estimating the scatter content in the acquired PET list-mode data through an analysis of the energy signals in the PET list-mode data and the modeled scattered radiation, in which the scattered and non-scattered radiation are represented by a combination of at least three basis functions; and (g) applying the estimated scatter content in the image reconstruction of the PET list-mode data, to obtain scatter-corrected image.

According to another aspect, a method for processing PET scan data is disclosed, where the method comprises: (a) acquiring scan data representative of a targeted patient tissue region using a PET scanner, wherein the scan data comprises PET list-mode data; (b) quantifying the distribution of energy signals in the PET list-mode data as 2D histograms representing A crystal energy vs. B crystal energy; (c) automatically estimating the scatter content in the acquired PET list-mode data through an analysis of the energy signals in the PET list-mode data and modeled scattered radiation acquired from a calibration of the PET scanner, in which the scattered and non-scattered radiation are represented by a combination of at least three basis functions; and (d) applying the estimated scatter content in the image reconstruction of the PET list-mode data, to obtain scatter-corrected image.

A PET scanner system comprising a processor configured to execute one or more embodiments of the disclosed methods is also provided.

A non-transitory computer-readable medium storing instructions configured to cause a computer system to execute one or more embodiments of the disclosed methods is also provided.

As long as the PET scanners record the energy spectra of both coincident photons with sufficient precision and the energy response is uniform across the scanner, and is stable over time and as count rates change, the methods disclosed herein can be implemented.

BRIEF DESCRIPTION OF THE DRAWINGS

The invention will now be more fully described by way of example with reference to the accompanying drawings in which.

DETAILED DESCRIPTION

This description of the exemplary embodiments is intended to be read in connection with the accompanying drawings, which are to be considered part of the entire written description. The disclosed embodiments are merely exemplary of the invention and the invention may be embodied in various and alternative forms. The schematic illustrations are not intended to show actual nor relative dimensions.

Figure 1:
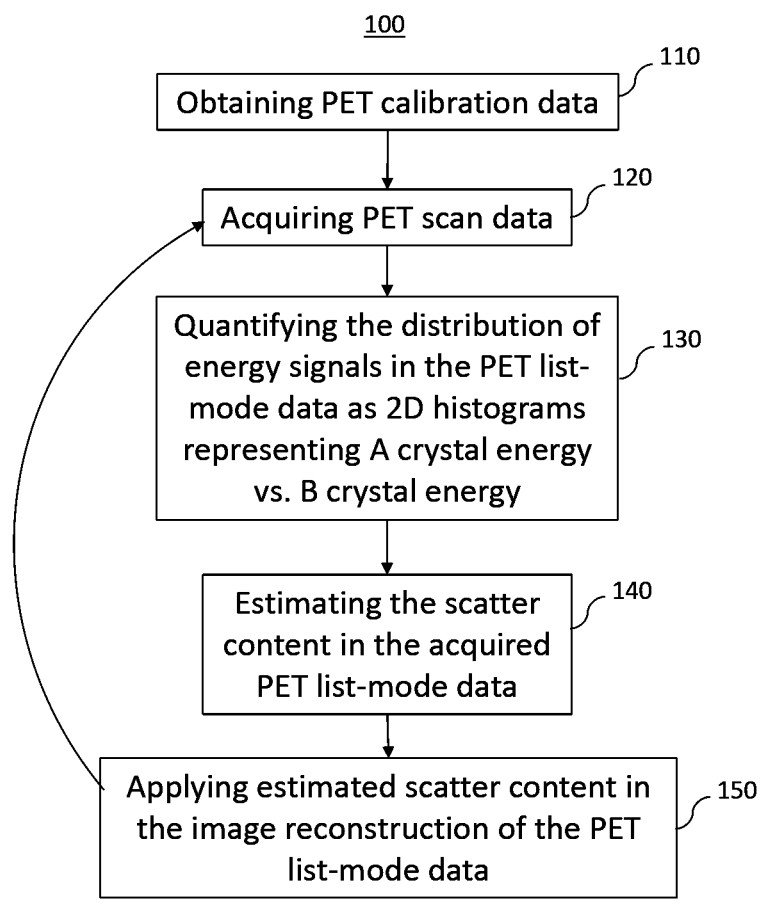
FIG. 1 is a flowchart of a method for processing PET scan data that comprises applying energy-based scatter correction according to the PET scan data according to the present disclosure.
Figure 2:
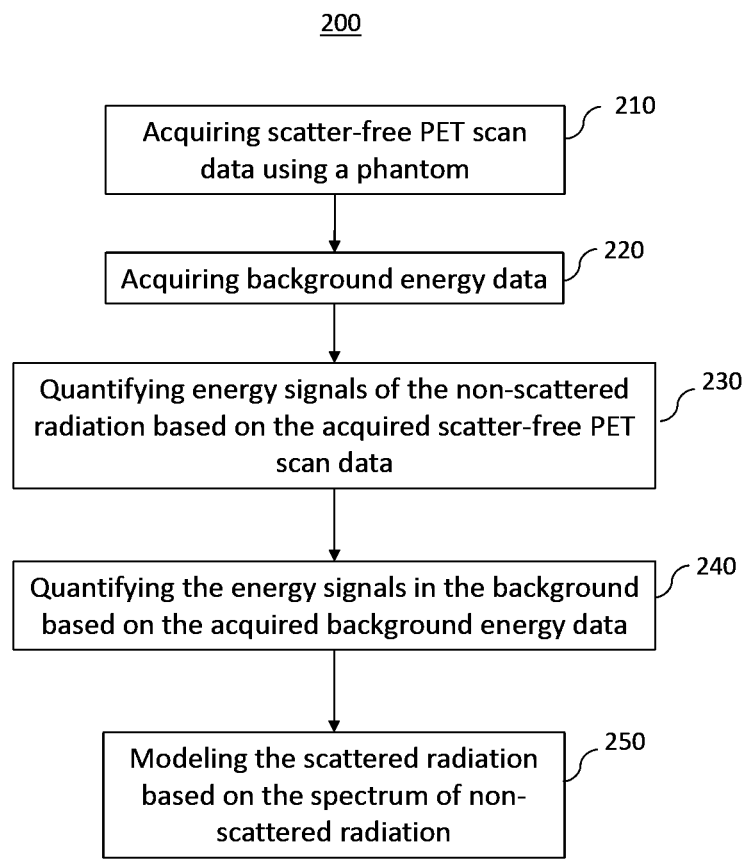
FIG. 2 is a flowchart of the method of applying the energy-based scatter correction to the PET scan data according to the present disclosure.

Referring to the flowchart 100 in FIG. 1, a method for processing positron emission tomography (PET) data that corrects for scatter of annihilation photons is provided. The method comprises obtaining PET calibration data (step 110); acquiring scan data representative of a targeted patient tissue region using a PET scanner, where the scan data comprises PET list-mode data, (step 120); quantifying the distribution of energy signals in the PET list-mode data as 2D histograms representing A crystal energy vs. B crystal energy, (step 130); automatically estimating the scatter content in the acquired PET list-mode data through an analysis of the energy signals in the PET list-mode data, in which the scattered and non-scattered radiation are represented by a combination of basis functions, (step 140); applying the estimated scatter content in image reconstruction of the PET list-mode data, (step 150). The reconstructed image is an image of the targeted patient tissue region in which the estimated scatter content has been removed. The arrow looping back to the step 120 indicates that the process can repeat to perform additional PET scans of the patient or a different patient reusing the calibration data without performing another calibration. The step 110 of obtaining PET calibration data is further elaborated as flowchart 200 in FIG. 2.

Referring to flowchart 200, a method for obtaining the PET calibration data is disclosed. The calibration procedure is for estimating scattered radiation in a PET scanner that records the energy of each detected annihilation photon, in the case when both scattered and non-scattered radiation is present. The method comprises: acquiring scatter-free PET scan data using a line source phantom in air or some other phantom that contains the radioactivity and stops the emitted positrons while scattering very little of the resulting annihilation radiation, where the PET scan data comprises PET list-mode data, (step 210); acquiring background energy data by performing a PET scan without any radiation source in the field-of-view of the PET scanner, (step 220); quantifying energy signals of the non-scattered radiation based on the acquired scatter-free PET scan, (step 230); quantifying the energy signals in the background based on the acquired background energy data, (step 240); and modeling the scattered radiation based on the spectrum of non-scattered radiation with a reduction of the energy signal and a modification to the spectrum's shape, (step 250). The step 230 comprises quantifying energy signals of the acquired scatter-free PET scan data as histograms.

Once PET scan data comprising list-mode data are acquired for a target patient tissue region, in order to estimate the necessary scatter correction, the list-mode data is treated as if the large groups of "A" and "B" scintillator crystals that generated the list-mode data are a single pseudo-supercrystal "A" and a single pseudo-supercrystal "B" so that sinograms could be made with millions of coincidences per energy bin. The actual PET scan uses smaller crystals but the invention uses the concept of pseudo-supercrystals, i.e. treats a collection of crystals as if they were a single detector, so as to increase the strength of the signal by counting more coincident photon pairs. This step is justified by the observation that scattered radiation is in most cases distributed smoothly in the space of the PET measurements, so a sampled representation based on pseudo-supercrystals is practical and adequate. As an example, when the crystals have dimensions 3×3 mm in cross section, one can group 10×10 of these into pseudo-supercrystals of size 30×30 mm, increasing the rate of coincidences by the fourth power of 10, i.e. 10,000.

Figure 4:
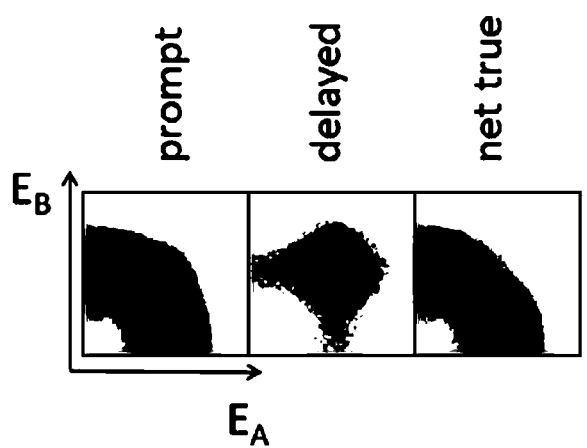
FIG. 4 shows 2D energy histograms $n(iE_A, iE_B)$ for prompt, delayed, and net-true coincidences.

Prompt PET events or coincidences occur when two energy-qualified photons are detected simultaneously in detector crystals identified as A and B. Delayed events or coincidences, also called random coincidences, occur when detector crystals A and B are in delayed coincidence. Both types of coincidences appear in the list-mode data, which identifies the A and B detector crystals, time of flight, information identifying prompt coincidences vs. random coincidences, and digitized energy signals. From this, the energy signals in the PET list-mode data are quantified by a 2-dimensional (2D) histogram $n(iE_A, iE_B)$, i.e., A crystal vs. B crystal energy histogram. This can be associated with any collection of coincident detector pairs, for example one A crystal and one B crystal, or a collection of 100 A crystals and 100 B crystals. FIG. 4 shows an example of such 2D histograms for a PET scan taken with a line source in a 20-cm cylinder in a sinogram region with high scatter content to simulate a patient. Net-true coincidences are the difference between prompt coincidences and random coincidences. A circular pattern near the center is the hallmark of non-scattered radiation, clearly seen in the random coincidence histogram. Low-energy tails indicate scatter.

The goal of scatter estimation is to quantify how much of the net-true data in any sinogram energy bin is due to scatter. In the energy-based approach of the present disclosure, this can be done in a 2D curve-fitting approach based on the 2D histograms. This seems possible in cases like FIG. 4 where the number of counts in the histogram was in the order of $10^7$, and the energy histograms are smooth with some added noise.

Calibration Procedure:

In order to apply energy-based scatter correction to actual PET sinogram data, a calibration data for the PET scanner is generated before a PET scan is performed on the target tissue region of the patient. The calibration comprises first acquiring scatter-free PET scan data using a line source phantom in air or some other phantom that contains the radioactivity and stops the emitted positrons while scattering very little of the resulting annihilation radiation, where the PET scan data comprises PET list-mode data. The emitted radiation from the line phantom is expected to scatter very little. This provides list-mode data containing energy spectrum of a known radiation source and functions as a fingerprint of the particular PET scanner's detectors as the list-mode data will not be tainted with scatter effects.

Next, the background energy data is acquired by performing a scan without any radiation source in the field of view of the PET scanner. The energy levels acquired during this background measurement will be largely due to beta decays of naturally occurring $^{176}$Lu in the LSO crystals.

Next, a model for non-scattered energy spectrum for the PET scanner is defined by calculating basis functions. One begins by considering a one-dimensional (1D) energy spectrum, $n(iE_A)$ or $n(iE_B)$, seen by just one detector or one group of detectors. The letters iE denote a bin or array location, appropriate for use in digital computers, that stores all energy values after conversion from analog to digital, and the distribution of energies is approximated by the set of all energy bins in the list-mode data. Monte-Carlo simulations suggested that, while the photopeak contribution should never change, the additive background of scatter should depend, with almost infinite variability, on the distribution of activity and the distribution of materials that scatter the radiation. This motivated the following 1D model:

$$n(iE) \approx \Sigma_{k=0}^{5} a_k p_k(iE). \quad (1)$$

That is, the non-scattered energy spectrum is modeled as a linear sum of six basis functions of energy in this example. Here, $p_0$ is the photopeak spectrum, $p_{1,2,3,4}$ model scatter through successively larger angles with a low-energy tail in each case, and $p_5$ models the spectrum above the photopeak. While $p_0$ has clear physical meaning, the main requirement in selecting $p_{1,2,3,4,5}$ is to provide a decent fit to spectra in the experiments. In the work described here, $p_0(iE)$ was taken directly from a measurement. It is the average spectrum of all detectors obtained from a scatter-free line-source during the calibration scan. The $p_1(iE)$ basis function was determined by selecting a sinogram region representing small-angle scatter in the case of a line source, and determining a smooth function f(iE) that closely fit the spectrum in this case, using the shape $p_1(iE)=p_0(f(iE))$.

Figure 5:
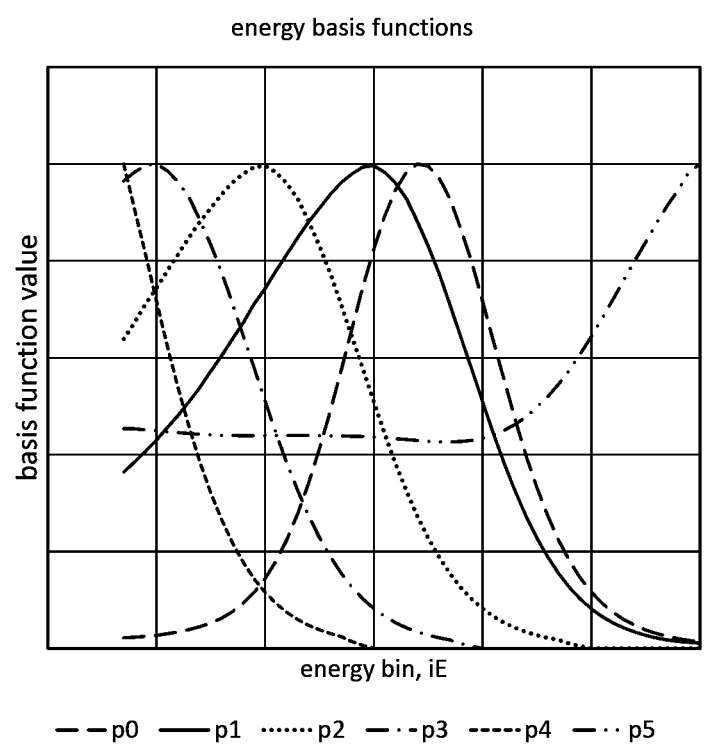
FIG. 5 represents a set of 1D energy basis functions $pk(iE)$, arbitrarily normalized.

The basis functions $p_2(iE)$, $p_3(iE)$, and $p_4(iE)$ were then determined by shifting $p_1(iE)$ downward in energy by successively larger amounts. The last basis function, $p_5(iE)$ represents the background energies detected by the detectors when no radiation source is present in the field of view. Without any radiation source in the field of view, the background energies detected are mainly due to beta decays of naturally occurring $^{176}$Lu in the LSO crystals. This background measurement can be taken during a calibration scan procedure. For example, a 2-hour scan can be taken without any radiation source in the field of view. The resulting basis functions are plotted in FIG. 5.

The basis functions are adjusted the magnitude of the basis functions according to the equation $\Sigma_{iE} p_k(iE)=1$ for each k.

Then, the noisy 2D histogram data is fit to a mathematical model by curve fitting. This is based on the 1D expansion described above. The 2D histogram is assumed to) be of the form $$n(iE_A, iE_B) = \Sigma a_{k_A k_B} p_{k_A}(iE_A) p_{k_B}(iE_B). \quad (2)$$

The expression in Equation (2) represent all the radiation measured, scattered and not scattered. It is an expansion with 36 terms, one of which represents the non-scattered part. The summation extends over $k_A$=0 to 5 and $k_B$=0 to 5, a total of 36 terms with known basis functions and unknown coefficients, $ak_A, k_B$. To determine these coefficients we use a maximum likelihood expectation maximization approach (ML-EM) as proposed by Popescu et al. (in "Model-based scatter correction for fully 3D PET," Phys. Med. Biol., vol. 51, pp. 2919-2937, 2006) in the simpler case of four unknowns. It is natural to use the familiar iterative solution described in 1982 by Shepp and Vardi (in "Maximum Likelihood reconstruction for emission tomography," IEEE Trans. Med. Im., vol. MI-1 no. 2, October 1982, pp. 113-122) for the different problem of PET image reconstruction. Each $ak_A, k_B$ was assigned a value of 1.0, then a solution was approached by iterating the equation $$a_{k_A k_B}^{new} = a_{k_A k_B}^{old} \times \sum_{iEA, iEB} \frac{n(iE_A, iE_B) p_{k_A}(iE_A) p_{k_B}(iE_B)}{\sum_{a_{k'_A k'_B}} a_{k'_A k'_B}^{old} p_{k'_A}(iEA) p_{k'_B}(iEB)}. \quad (3)$$

This comparatively small ML-EM calculation is used in each sinogram energy bin. The analogy to image reconstruction is as follows. The measured $n(iE_A, iE_B)$ values play the role of the sinogram in image reconstruction; coefficients $ak_A, k_B$ play the role of image pixel values; basis functions $p_{kA}(iE_A) p_{kB}(iE_B)$ play the role of the transition matrix, with unit normalization assumed here and in the Shepp-Vardi paper; and the ML-EM formalism, and this update equation, are applicable because a Poisson model was assumed by Shepp and Vardi and is expected to apply just as well for a modern PET scanner with coincidence events reported in each energy bin and for each crystal, or for any group of crystals. Equation (3) should be used separately for prompt and delayed coincidences, since these do follow the Poisson model whereas other things do not, like the net-true counts. In one example, the equation (3) was iterated 50 times.

Scatter Estimate Model:

In estimating the number of coincidences resulting from scatter, TOF and non-TOF cases differ. In prompt or delayed coincidences, the estimated number of non-scattered coincidences is $a_{00}$. The estimated number of scattered coincidences in the sinogram energy bin is the difference between all net-true counts in the bin, and $a_{00}$. In the non-TOF case, the scatter estimate is $$s = N \times (n - (a_{00}(\text{prompt}) - a_{00}(\text{delayed}))), \quad (4)$$

where N is the PET normalization coefficient for the sinogram energy bin and n is the total number of net-true coincidences in the bin. For a TOF sinogram energy bin when the total number of time bins is nTOF, the same delayed coincidences are used for each time bin and the corresponding equation is $$s = N \times \left( n - \left( a_{00}(\text{prompt}) - \frac{a_{00}(\text{delayed})}{n_{TOF}} \right) \right). \quad (5)$$

The scatter calculation, i.e. the solution to equation (2), is made twice for each pixel: once for prompt coincidences and once for delayed coincidences.

Scatter Estimation in Actual PET Sinogram:

Above approach, described for one sinogram energy bin, can now be used to estimate scatter in an entire sinogram of an actual PET scan data. We assume that the scattered radiation is distributed very smoothly. Having assumed this, it is reasonable to assume very large detectors by grouping many A crystals and many B crystals and treat them as pseudo-supercrystals as discussed above.

Figure 3:
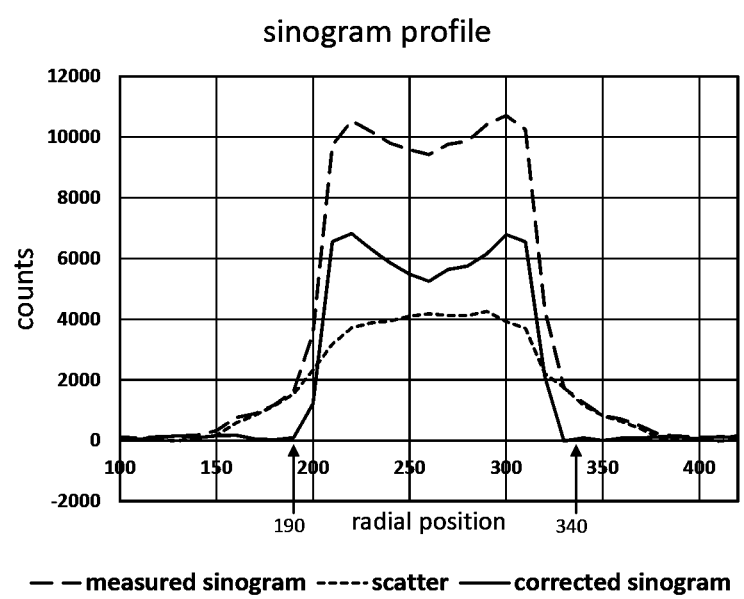
FIG. 3 shows a sinogram profile that has been segregated into the measured total sinogram, the scatter component sinogram, and the corrected sinogram where the scatter component has been removed.

FIG. 3 shows a sinogram profile that has been segregated into the measured total sinogram, the scatter component sinogram, and the corrected sinogram where the scatter component has been removed.

Based on the above discussion, a method for processing PET scan data includes estimating energy-based scattered radiation in a PET scanner that records the energy of each detected annihilation photon, in the case when both scattered and non-scattered radiation is present, by: (a) acquiring scatter-free PET scan data using a substantially scatter-free source phantom in air, wherein the PET scan data comprises PET list-mode data; (b) quantifying energy signals of the non-scattered radiation based on the acquired scatter-free PET scan data; and (c) modeling the scattered radiation based on the spectrum of non-scattered radiation with a reduction of the energy signal and a modification to the spectrum's shape. Then, the method for processing PET scan data further includes: (d) acquiring scan data representative of a targeted patient tissue region using a PET scanner, wherein the scan data comprises PET list-mode data; (e) quantifying the distribution of energy signals in the PET list-mode data as 2D histograms representing A crystal energy vs. B crystal energy; (f) automatically estimating the scatter content in the acquired PET list-mode data through an analysis of the energy signals in the PET list-mode data and the modeled scattered radiation, in which the scattered and non-scattered radiation are represented by a combination of at least three basis functions; and (g) applying the estimated scatter content in the image reconstruction of the PET list-mode data, to obtain scatter-corrected image. The steps (d) through (g) can be repeated for another PET scan of the targeted patient tissue region or a PET scan of a different targeted patient tissue region.

In some embodiments, the method can further comprise acquiring background energy data by performing a PET scan without any radiation source in the field-of-view of the PET scanner; and quantifying the energy signals in the background based on the acquired background energy data.

In some embodiments of the method, the step (b) comprises quantifying energy signals in the acquired scatter-free PET scan data as histograms of energy signals, and step (f) comprises curve fitting the scan-data energy histograms in an expansion with at least 3 basis functions for A crystals and at least 3 basis functions for B crystals. In some embodiments, the curve fitting of the 2D energy histograms is in an expansion with 6 basis functions for A crystals and 6 basis functions for B crystals.

In some embodiments of the method, the PET scanner is a TOF PET scanner and the PET list-mode data is TOF PET list-mode data, where the step (g) comprises subtracting estimated scatter coincidences from each of the sinogram energy bins in the TOF PET list-mode data, where the estimated scatter coincidences "s" in a sinogram bin is determined by the equation (4).

In some embodiments of the method, the PET scanner is a non-TOF PET scanner, where the step (g) comprises subtracting estimated scatter coincidences from each of the sinogram energy bins in the PET list-mode data, where the estimated scatter coincidences "s" in a sinogram bin is determined by the equation (5).

In another embodiment of the present disclosure, a method for processing PET scan data comprises: (aa) acquiring scan data representative of a targeted patient tissue region using a PET scanner, wherein the scan data comprises PET list-mode data; (bb) quantifying the distribution of energy signals in the PET list-mode data as 2D histograms representing A crystal energy vs. B crystal energy; (cc) automatically estimating the scatter content in the acquired PET list-mode data through an analysis of the energy signals in the PET list-mode data and modeled scattered radiation acquired from a calibration of the PET scanner, in which the scattered and non-scattered radiation are represented by a combination of at least three basis functions; and (dd) applying the estimated scatter content in the image reconstruction of the PET list-mode data, to obtain scatter-corrected image.

In some embodiments of the method, the step (bb) comprises curve fitting the 2D histograms in an expansion with at least 3 basis functions for A crystals and at least 3 basis functions for B crystals. In some embodiments, the step (bb) comprises curve fitting the 2D histograms is in an expansion with 6 basis functions for A crystals and 6 basis functions for B crystals.

In some embodiments, the PET scanner is a TOF PET scanner and the PET list-mode data is TOF PET list-mode data, where the step (dd) comprises subtracting estimated scatter coincidences from each of the sinogram energy bins in the TOF PET list-mode data, wherein the estimated scatter coincidences "s" in a sinogram bin is determined by the equation (4).

In some embodiments, the PET scanner is a non-TOF PET scanner, where the step (dd) comprises subtracting estimated scatter coincidences from each of the sinogram energy bins in the TOF PET list-mode data, wherein the estimated scatter coincidences "s" in a sinogram bin is determined by the equation (5).

Figure 6:
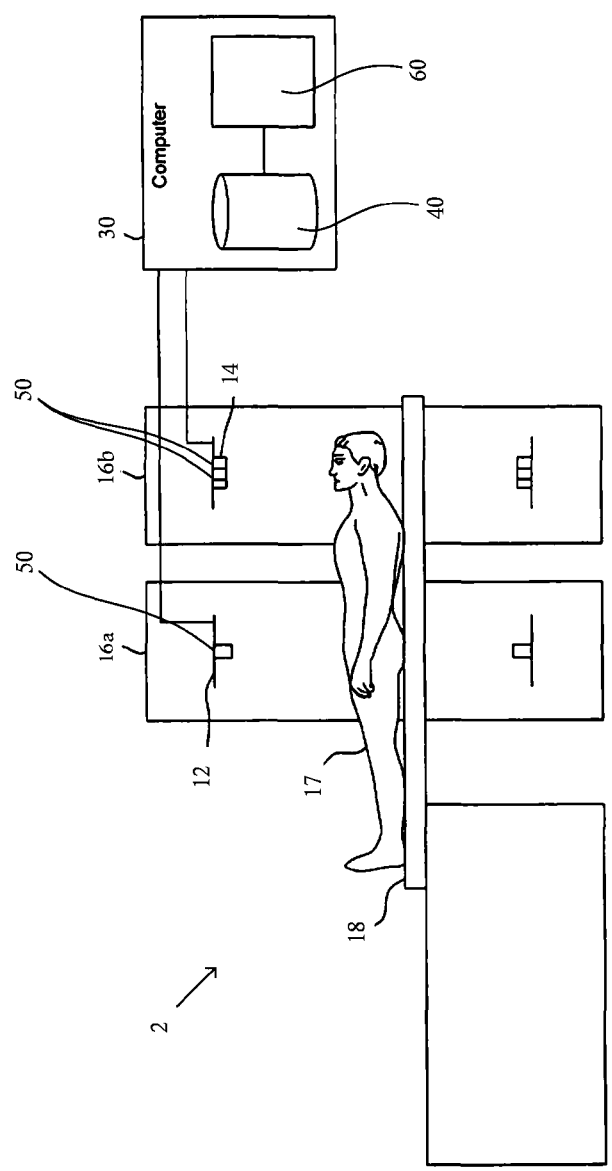
FIG. 6 is a schematic illustration of a PET scanner system.

According to another aspect of the present disclosure, FIG. 6 illustrates one embodiment of a nuclear imaging system 2 that is configured for implementing the methods disclosed herein. The nuclear imaging system 2 includes a scanner for a PET modality 12 provided in a first gantry 16a. A patient 17 lies on a movable patient bed 18 that can be movable with respect to the first gantry 16a. The PET modality 12 includes a plurality of detectors 50 configured to detect an annihilation photons.

Scan data from the PET modality 12 is stored at one or more computer databases 40 and processed by one or more computer processors 60 of an accompanying computer system 30. The graphical depiction of the computer system 30 in FIG. 6 is provided by way of illustration only, and the computer system 30 may include one or more separate computing devices. The scan data can be provided by the PET modality 12, the second modality 14, and/or may be provided as a separate data set, such as, for example, from a memory coupled to the computer system 30. The computer system 30 can include one or more processing electronics for processing a signal received from the detectors 50.

The methods and system described herein can be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

According to some embodiments, the nuclear imaging system 2 is a PET scanner system comprising a processor 60 configured to: (a) acquire scan data representative of a targeted patient tissue region using a PET scanner, wherein the scan data comprises PET list-mode data; (b) quantify the distribution of energy signals in the PET list-mode data as 2D histograms representing A crystal energy vs. B crystal energy; (c) automatically estimate the scatter content in the acquired PET list-mode data through an analysis of the energy signals in the PET list-mode data, in which the scattered and non-scattered radiation are represented by a combination of at least three basis functions; and (d) apply the estimated scatter content in the image reconstruction of the PET list-mode data, to obtain scatter-corrected image. In some embodiments, the 2D histograms of A crystal energy and B crystal energy represent 2D histograms of energy signals of all A crystals in the PET list-mode data and energy signals of all B crystals in the PET list-mode data.

In some embodiments of the PET scanner system 2, the step (b) comprises curve fitting the 2D histograms in an expansion with at least 3 basis functions for A crystals and at least 3 basis functions for B crystals. In some embodiments, the step (b) comprises curve fitting the 2D histograms in an expansion with 6 basis functions for A crystals and 6 basis functions for B crystals.

In some embodiments of the PET scanner system 2, the PET scanner is a TOF PET scanner and the PET list-mode data is TOF PET list-mode data, wherein applying estimated scatter content in the image reconstruction of the PET list-mode data comprises subtracting estimated scatter coincidences from each of the sinogram energy bins in the TOF PET list-mode data, wherein the estimated scatter coincidences "s" in a sinogram bin is determined by the equation (4).

In some embodiments of the PET scanner system 2, the PET scanner is a non-time-of-flight PET scanner, wherein applying the estimated scatter content in the image reconstruction of the PET list-mode data comprises subtracting estimated scatter coincidences from each of the sinogram energy bins in the PET list-mode data, wherein the estimated scatter coincidences "s" in a sinogram bin is determined by the equation (5).

In some embodiments, at least one non-transitory computer-readable storage medium is provided having computer-executable instructions embodied thereon, wherein, when executed by at least one processor 60, the computer-executable instructions cause the at least one processor to execute the steps of: (a) acquiring scan data representative of a targeted patient tissue region using a PET scanner, wherein the scan data comprises PET list-mode data; (b) quantifying the distribution of energy signals in the PET list-mode data as 2D histograms representing A crystal energy vs. B crystal energy; (c) automatically estimating the scatter content in the acquired PET list-mode data through an analysis of the energy signals in the PET list-mode data, in which the scattered and non-scattered radiation are represented by a combination of at least three basis functions; and (d) applying the estimated scatter content in the image reconstruction of the PET list-mode data, to obtain scatter-corrected image.

In some embodiments of the non-transitory computer-readable storage medium, the 2D histograms of A crystal energy and B crystal energy represent 2D histograms of energy signals of all A crystals in the PET list-mode data and energy signals of all B crystals in the PET list-mode data.

In some embodiments of the non-transitory machine readable storage medium, the step (b) comprises curve fitting the 2D histograms in an expansion with at least 3 basis functions for A crystals and at least 3 basis functions for B crystals. In some embodiments, the step (b) comprises curve fitting the 2D histograms is in an expansion with 6 basis functions for A crystals and 6 basis functions for B crystals.

Although the subject matter has been described in terms of exemplary embodiments, it is not limited thereto. Rather, the appended claims should be construed broadly, to include other variants and embodiments, which may be made by those skilled in the art.

What is claimed is:

1. A method of estimating scattered radiation in a positron emission tomography (PET) scanner that records the energy of each detected photon, in the case when both scattered and non-scattered radiation is present, the method comprising: (a) acquiring scatter-free PET scan data using a substantially scatter-free source phantom in air, wherein the PET scan data comprises PET list-mode data; (b) quantifying energy signals of the non-scattered radiation based on the acquired scatter-free PET scan data; (c) modeling the scattered radiation based on the spectrum of non-scattered radiation with a reduction of the energy signal and a modification to the spectrum's shape; (d) acquiring scan data representative of a targeted patient tissue region using a PET scanner, wherein the scan data comprises PET list-mode data; (e) quantifying the distribution of energy signals in the PET list-mode data as 2D histograms representing A crystal energy vs. B crystal energy; (f) automatically estimating the scatter content in the acquired PET list-mode data through an analysis of the energy signals in the PET list-mode data and the modeled scattered radiation, in which the scattered and non-scattered radiation are represented by a combination of at least three basis functions; and (g) applying the estimated scatter content in the image reconstruction of the PET list-mode data, to obtain scatter-corrected image.

2. The method of claim 1, further comprising acquiring background energy data by performing a PET scan without any radiation source in the field-of-view of the PET scanner; and quantifying the energy signals in the background based on the acquired background energy data.

3. The method of claim 1, wherein the step (b) comprises quantifying energy signals in the acquired scatter-free PET scan data as histograms of energy signals, and step (f) comprises curve fitting the scan-data energy histograms in an expansion with at least 3 basis functions for A crystals and at least 3 basis functions for B crystals.

4. The method of claim 3, wherein the curve fitting of the 2D energy histograms is in an expansion with 6 basis functions for A crystals and 6 basis functions for B crystals.

5. The method of claim 1, wherein the steps (d) through (g) are repeated for another PET scan of the targeted patient tissue region or a PET scan of a different targeted patient tissue region.

6. The method of claim 1, wherein the PET scanner is a time-of-flight (TOF) PET scanner and the PET list-mode data is TOF PET list-mode data, wherein applying the estimated scatter content in the image reconstruction of the PET list-mode data comprises subtracting estimated scatter coincidences from each of the sinogram energy bins in the TOF PET list-mode data, wherein the estimated scatter coincidences "s" in a sinogram bin is determined by $$s = N \times \left(n - \left(a_{00}(\text{prompt}) - \frac{a_{00}(\text{delayed})}{n_{TOF}}\right)\right),$$

wherein,
N is PET normalization coefficient for each sinogram energy bin, n is the total number of net-true coincidences in each sinogram energy bin, $a_{00}$ is the estimated number of non-scattered coincidences in each sinogram energy bin, prompt is the number of prompt coincidences in each sinogram energy bin, delayed is the number of delayed coincidences in each sinogram energy bin, and $n_{TOF}$ is the total number of time bins.

7. The method of claim 1, wherein the PET scanner is a non-time-of-flight PET scanner, wherein applying the estimated scatter content in the image reconstruction of the PET list-mode data comprises subtracting estimated scatter coincidences from each of the sinogram energy bins in the PET list-mode data, wherein the estimated scatter coincidences "s" in a sinogram bin is determined by $$s = N \times (n - (a_{00}(\text{prompt}) - a_{00}(\text{delayed}))),$$

wherein, N is PET normalization coefficient for each sinogram energy bin, n is the total number of net-true coincidences in each sinogram energy bin, $a_{00}$ is the estimated number of non-scattered coincidences in each sinogram energy bin, prompt is the number of prompt coincidences in each sinogram energy bin, and delayed is the number of delayed coincidences in each sinogram energy bin.

8. A method for processing positron emission tomography (PET) scan data, comprising:
(a) acquiring scan data representative of a targeted patient tissue region using a PET scanner, wherein the scan data comprises PET list-mode data;
(b) quantifying the distribution of energy signals in the PET list-mode data as 2D histograms representing A crystal energy vs. B crystal energy;
(c) automatically estimating the scatter content in the acquired PET list-mode data through an analysis of the energy signals in the PET list-mode data and modeled scattered radiation acquired from a calibration of the PET scanner, in which the scattered and non-scattered radiation are represented by a combination of at least three basis functions; and (d) applying the estimated scatter content in the image reconstruction of the PET list-mode data, to obtain scatter-corrected image.

9. The method of claim 8, wherein the step (b) comprises curve fitting the 2D histograms in an expansion with at least 3 basis functions for A crystals and at least 3 basis functions for B crystals.

10. The method of claim 8, wherein the step (b) comprises curve fitting the 2D histograms is in an expansion with 6 basis functions for A crystals and 6 basis functions for B crystals.

11. The method of claim 8, wherein the PET scanner is a time-of-flight (TOF) PET scanner and the PET list-mode data is TOF PET list-mode data, wherein applying the estimated scatter content in the image reconstruction of the PET list-mode data comprises subtracting estimated scatter coincidences from each of the sinogram energy bins in the TOF PET list-mode data, wherein the estimated scatter coincidences "s" in a sinogram bin is determined by $$s = N \times \left( n - \left( a_{00}(\text{prompt}) - \frac{a_{00}(\text{delayed})}{n_{TOF}} \right) \right),$$

wherein,
N is PET normalization coefficient for each sinogram energy bin, n is the total number of net-true coincidences in each sinogram energy bin, $a_{00}$ is the estimated number of non-scattered coincidences in each sinogram energy bin, prompt is the number of prompt coincidences in each sinogram energy bin, delayed is the number of delayed coincidences in each sinogram energy bin, and $n_{TOF}$ is the total number of time bins.

12. The method of claim 8, wherein the PET scanner is a non-time-of-flight PET scanner,
wherein applying the estimated scatter content in the image reconstruction of the PET list-mode data comprises subtracting estimated scatter coincidences from each of the sinogram energy bins in the PET list-mode data, wherein the estimated scatter coincidences "s" in a sinogram bin is determined by $$s = N \times (n - (a_{00}(\text{prompt}) - a_{00}(\text{delayed}))),$$

wherein, N is PET normalization coefficient for each sinogram energy bin, n is the total number of net-true coincidences in each sinogram energy bin, $a_{00}$ is the estimated number of non-scattered coincidences in each sinogram energy bin, prompt is the number of prompt coincidences in each sinogram energy bin, and delayed is the number of delayed coincidences in each sinogram energy bin.

13. The method of claim 8, wherein the calibration of the PET scanner comprises:
acquiring scatter-free PET scan data using a substantially scatter-free source phantom in air, wherein the PET scan data comprises PET list-mode data; quantifying energy signals of the non-scattered radiation based on the acquired scatter-free PET scan data; and
modeling the scattered radiation based on the spectrum of non-scattered radiation with a reduction of the energy signal and a modification to the spectrum's shape.

14. A positron emission tomography (PET) scanner system comprising: a processor configured to: (a) acquire scan data representative of a targeted patient tissue region using a PET scanner, wherein the scan data comprises PET list-mode data;
(b) quantify the distribution of energy signals in the PET list-mode data as 2D histograms representing A crystal energy vs. B crystal energy;
(c) automatically estimate the scatter content in the acquired PET list-mode data through an analysis of the energy signals in the PET list-mode data and modeled scattered radiation acquired from a calibration of the PET scanner, in which the scattered and non-scattered radiation are represented by a combination of at least three basis functions; and (d) apply the estimated scatter content in the image reconstruction of the PET list-mode data, to obtain scatter-corrected image.

15. The PET scanner system of claim 14, wherein the 2D histograms of A crystal energy and B crystal energy represent 2D histograms of energy signals of all A crystals in the PET list-mode data and energy signals of all B crystals in the PET list-mode data.

16. The PET scanner system of claim 14, wherein the step (b) comprises curve fitting the 2D histograms in an expansion with at least 3 basis functions for A crystals and at least 3 basis functions for B crystals.

17. The PET scanner system of claim 14, wherein the step (b) comprises curve fitting the 2D histograms in an expansion with 6 basis functions for A crystals and 6 basis functions for B crystals.

18. The PET scanner system of claim 14, wherein the PET scanner is a time-of-flight (TOF) PET scanner and the PET list-mode data is TOF PET list-mode data, wherein applying the estimated scatter content in the image reconstruction of the PET list-mode data comprises subtracting estimated scatter coincidences from each of the sinogram energy bins in the TOF PET list-mode data, wherein the estimated scatter coincidences "s" in a sinogram bin is determined by $$s = N \times \left( n - \left( a_{00}(\text{prompt}) - \frac{a_{00}(\text{delayed})}{n_{TOF}} \right) \right),$$

wherein, N is PET normalization coefficient for each sinogram energy bin, n is the total number of net-true coincidences in each sinogram energy bin, $a_{00}$ is the estimated number of non-scattered coincidences in each sinogram energy bin, prompt is the number of prompt coincidences in each sinogram energy bin, delayed is the number of delayed coincidences in each sinogram energy bin, and $n_{TOF}$ is the total number of time bins.

19. The PET scanner system of claim 14, wherein the PET scanner is a non-time-of-flight PET scanner, wherein applying the estimated scatter content in the image reconstruction of the PET list-mode data comprises subtracting estimated scatter coincidences from each of the sinogram energy bins in the PET list-mode data, wherein the estimated scatter coincidences "s" in a sinogram bin is determined by $$s = N \times (n - (a_{00}(\text{prompt}) - a_{00}(\text{delayed}))),$$

wherein, N is PET normalization coefficient for each sinogram energy bin, n is the total number of net-true coincidences in each sinogram energy bin, $a_{00}$ is the estimated number of non-scattered coincidences in each sinogram energy bin, prompt is the number of prompt coincidences in each sinogram energy bin, and delayed is the number of delayed coincidences in each sinogram energy bin.

20. The PET scanner system of claim 14, wherein the calibration of the PET scanner comprises: acquiring scatter-free PET scan data using a substantially scatter-free source phantom in air, wherein the PET scan data comprises PET list-mode data; quantifying energy signals of the non-scattered radiation based on the acquired scatter-free PET scan data; and
modeling the scattered radiation based on the spectrum of non-scattered radiation with a reduction of the energy signal and a modification to the spectrum's shape.

21. A non-transitory computer-readable storage medium storing instructions configured to cause a computer system to execute the steps of:

(a) acquiring scan data representative of a targeted patient tissue region using a PET scanner, wherein the scan data comprises PET list-mode data;
(b) quantifying the distribution of energy signals in the PET list-mode data as 2D histograms representing A crystal energy vs. B crystal energy;
(c) automatically estimating the scatter content in the acquired PET list-mode data through an analysis of the energy signals in the PET list-mode data and modeled scattered radiation acquired from a calibration of the PET scanner, in which the scattered and non-scattered radiation are represented by a combination of at least three basis functions; and (d) applying the estimated scatter content in the image reconstruction of the PET list-mode data, to obtain scatter-corrected image.

22. The non-transitory computer-readable storage medium of claim 21, wherein the 2D histograms of A crystal energy and B crystal energy represent 2D histograms of energy signals of all A crystals in the PET list-mode data and energy signals of all B crystals in the PET list-mode data.

23. The non-transitory computer-readable storage medium of claim 21, wherein the step (b) comprises curve fitting the 2D histograms in an expansion with at least 3 basis functions for A crystals and at least 3 basis functions for B crystals.

24. The non-transitory computer-readable storage medium of claim 21, wherein the step (b) comprises curve fitting the 2D histograms in an expansion with 6 basis functions for A crystals and 6 basis functions for B crystals.

25. The non-transitory computer-readable storage medium of claim 21, wherein the calibration of the PET scanner comprises: acquiring scatter-free PET scan data using a substantially scatter-free source phantom in air, wherein the PET scan data comprises PET list-mode data; quantifying energy signals of the non-scattered radiation based on the acquired scatter-free PET scan data; and modeling the scattered radiation based on the spectrum of non-scattered radiation with a reduction of the energy signal and a modification to the spectrum's shape.

* * * * *